(12) United States Patent
Reider (10) Patent No.: US 10,307,589 B2
(45) Date of Patent: Jun. 4, 2019

(54) INTERACTIVE MUSCLE TRAINING DEVICE AND METHOD

(71) Applicant: Brent C. Reider, Oxford, OH (US)

(72) Inventor: Brent C. Reider, Oxford, OH (US)

( * ) Notice: Subject to any disclaimer, the term of this patent is extended or adjusted under 35 U.S.C. 154(b) by 145 days.

(21) Appl. No.: 15/010,372

(22) Filed: Jan. 29, 2016

(65) Prior Publication Data
US 2017/0216588 A1   Aug. 3, 2017

(51) Int. Cl.
*A61N 1/36* (2006.01)
*A61N 1/05* (2006.01)
*A63F 13/285* (2014.01)

(52) U.S. Cl.
CPC ........... *A61N 1/36007* (2013.01); *A61N 1/05* (2013.01); *A61N 1/36014* (2013.01); *A63F 13/285* (2014.09)

(58) Field of Classification Search
CPC .................. A61N 1/36014; A61N 1/36003
See application file for complete search history.

(56) References Cited

U.S. PATENT DOCUMENTS

| | | | |
|---|---|---|---|
| 5,041,974 A * | 8/1991 | Walker | A61N 1/08 607/48 |
| 9,173,806 B1 | 11/2015 | Dematio et al. | |
| 9,372,533 B1 * | 6/2016 | Agrama | A63F 13/06 |
| 2010/0304864 A1 | 12/2010 | Johnson et al. | |
| 2013/0066400 A1 * | 3/2013 | Perryman | A61N 1/37229 607/59 |
| 2013/0337975 A1 * | 12/2013 | Yanev | A61N 1/36003 482/8 |
| 2014/0057232 A1 * | 2/2014 | Wetmore | G09B 19/00 434/236 |
| 2014/0200432 A1 * | 7/2014 | Banerji | A61B 5/0488 600/383 |
| 2014/0249602 A1 * | 9/2014 | Colborn | A61N 1/36053 607/59 |

OTHER PUBLICATIONS

Laborie Medical Technologies, Pelvic Floor Therapy—Biofeedback and More: Conservative Treatment for Pelvic Floor Disorders, retrieved from website Dec. 9, 2015, www.laborie.com.

* cited by examiner

*Primary Examiner* — George R Evanisko
(74) *Attorney, Agent, or Firm* — Standley Law Group LLP (57) ABSTRACT

The present invention is a system and method for providing an electrical stimulation signal to condition the pelvic wall muscles of a user and demonstrate to the user the proper muscle usage. The system and method also provides a system for measuring the users muscle response. The system and method also provides an entertaining interaction environment which encourages the user to perform self-initiated conditioning exercises.

7 Claims, 11 Drawing Sheets

INTERACTIVE MUSCLE TRAINING DEVICE AND METHOD

TECHNICAL FIELD

Exemplary embodiments of the present invention relate generally to devices for conditioning and training the muscle response of certain muscles in humans including the muscles of the pelvic floor in female subjects.

BACKGROUND AND SUMMARY OF THE INVENTION

In human females, the pelvic floor muscles may become weak or lose conditioning as the result of age, childbirth, injury or disease. As a result, those with weak or unconditioned muscles may experience difficulty controlling or stopping the flow of urine. As a result, these individuals may experience episodes of incontinence or other undesirable situations related to muscle control. In order to improve the condition of the pelvic floor muscles and thus reduce the incidences of incontinence, individuals may perform various exercises including an exercise that involves the voluntary contraction of the pelvic floor muscles. The most well-known of these is the Kegel exercise. When performing Kegel exercises, a subject generally will attempt to contract their muscles for a short period of time, release the contraction of those muscles and then repeat this process. The desired result is the improvement of muscle tone in the pelvic floor muscles. Some individuals may have difficulty identifying the correct muscles to contract or may not hold the contraction long enough to be beneficial. In other cases, the individual may not remember to perform the exercises or lose interest and either stop performing the exercise or not perform them frequently enough to obtain a desired benefit. There have been devices disclosed that assist a user in their efforts to learn to contract the muscles of the pelvic floor using various methods of electrically stimulating those muscles. In fact, various classes of muscle stimulators have been defined by the U.S. Food and Drug Administration including muscle stimulators for the improvement of muscle tone, muscle stimulators for the treatment of incontinence and stimulation for the treatment of muscle pain. Devices for facilitating some of these treatments are also known in the art. For example, U.S. Pat. No. 5,800,501 (Sherlock) discloses a device for providing an electrode for electrical stimulation. This same device may also be used to receive biofeedback signals. With such a device, a user may receive stimulation in order to strengthen the muscles of the pelvic floor. In addition to the stimulation portions, Sherlock also discloses a biofeedback portion. The biofeedback portion may be used to measure a user's muscle activity in response to such stimulation or as the result of exercises initiated by the user. Such a device may be of value to a user who desires to strengthen their pelvic floor muscles by combining stimulation with self-initiated muscle exercise. A user of such a device must be diligent with regard to their self-initiated exercises in order to see optimum results with regard to muscle strengthening. The use of games or similar methods of engaging a user may be beneficial in that such methods may encourage the user to persist in their exercise program. Various classes of muscle stimulators have been defined by the U.S. Food and Drug Administration including muscle stimulators for the improvement of muscle tone, muscle stimulators for the treatment of incontinence and stimulation for the treatment of muscle pain. What is needed is a device and method of using such a device that encourages a user to engage in muscle conditioning exercises through the use of stimulation and biofeedback combined with an interactive game.

In an embodiment of such a device and system, a muscle stimulation system may be combined with a biofeedback receiving system that interacts with a plurality of games. A user of such a device may engage the muscle stimulation system to both provide conditioning to pelvic floor muscles and also to learn what sort of muscle response produces the desired conditioning of the pelvic floor muscles. A user may also use the plurality of games to encourage the user to perform exercises to strengthen the pelvic floor muscles. Games may have the benefit of encouraging the user to initiate the desired exercise and also to provide guidance to the user in regards to an optimum exercise level and technique. In an embodiment of the invention, a firewall may be created between the stimulation portion and the feedback portion to prevent the use of the feedback portion to control the stimulation. Such a firewall may be physical in nature, in other words, a physical isolation between the electronic components comprising the stimulation and biofeedback portion of an embodiment of the invention. In other embodiments of the invention, the firewall may be formed by the software programming of the embodiment. In such an example, the software may be designed to prevent interaction between the biofeedback and stimulation portions of the embodiment. In an embodiment of the device in which the firewall is formed in software, an enabling code may be implemented such that persons seeking to change or modify the device programming may be prevented from doing so without having the proper enabling code. Such an enabling code feature may also be used to prevent software modifications or game designs that may be harmful to a user of the device.

Further features and advantages of the devices and systems disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Figure 1:
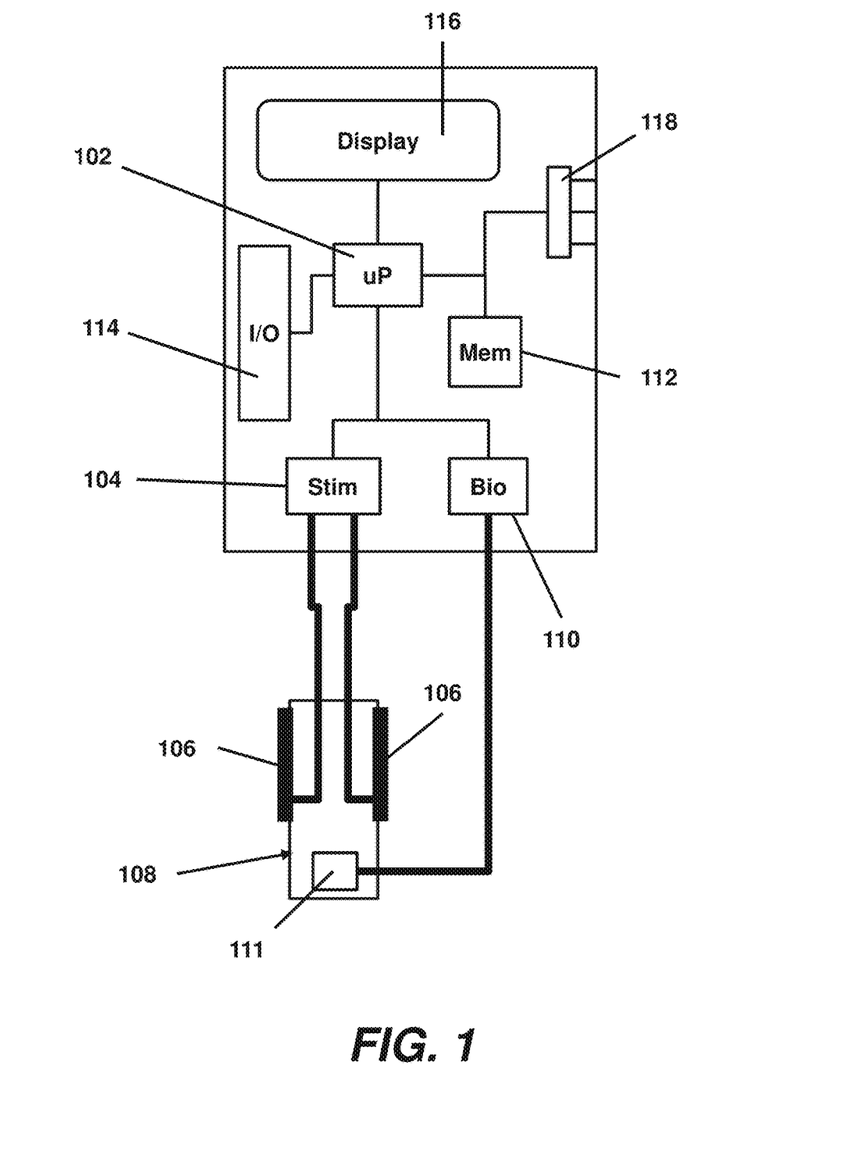
FIG. 1 is a block diagram of an embodiment of the invention.

Referring to FIG. 1, an embodiment of the invention may comprise a processor 102 that is in electronic communication with a stimulator 104. In such an embodiment the stimulator may be in electronic communication with a plurality of electrodes 106. In certain embodiments of the invention, these electrodes may be mounted to a probe device 108 that is configured to position the electrodes correctly when in use. In the illustrated embodiment, the processor 102 may also be in electronic communication with a biofeedback receiver 110. The biofeedback receiver may in turn be in electronic communication with a transducer 111. As shown, the transducer may be incorporated into the probe 108. Other embodiments may provide a transducer as a separate component to be used either in conjunction with the probe or separately when stimulation is not required. In embodiments of the invention, the transducer may be configured to receive electrical signals that are produced by the body when muscles contract. Other embodiments may use various pressure sensors to detect contraction of muscles against the transducer.

As illustrated, the processor 102 may be in electrical communication with a memory 112, an input/output (I/O) section 114 which may comprise such inputs as pushbuttons, sound devices, or other selector devices and input/outputs such as Wi-Fi and other wired or wireless data connections, a display 116, and an external display interface 118. The external display interface may comprise wired and wireless connections to permit embodiments of the invention to communicate to external displays in order to enhance the user's interactions with the device.

Figure 2:
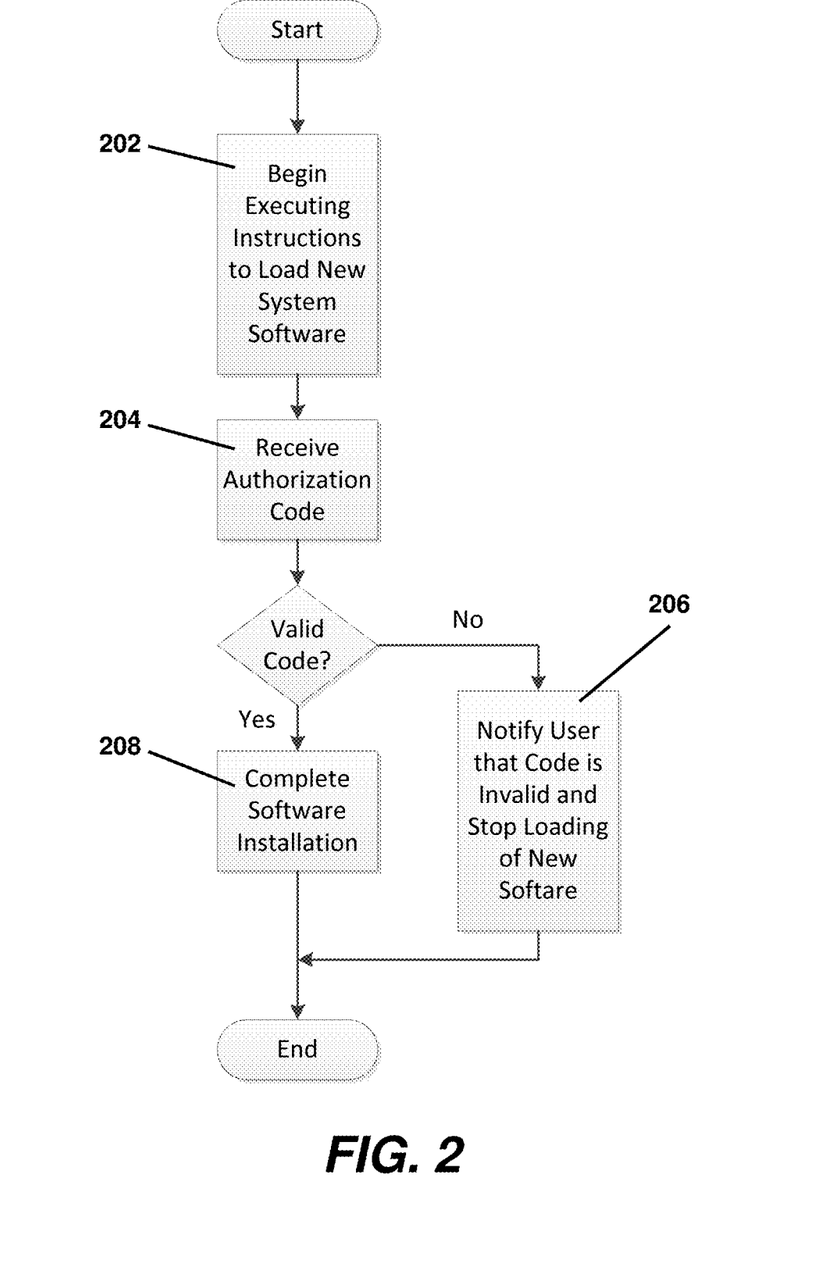
FIG. 2 is a flow chart of the steps performed to verify authorization to reprogram certain functions of an embodiment of the invention.

In embodiments of the invention, the memory 112 may be electronically programmable to permit the function of the device to be modified. Such programming may be done with the memory in place via a connection to the I/O section 114 or may be performed externally and written to a memory device that may then be physically inserted into the device such that the memory device is placed in electrical communication with the processor 102. In order to insure device safety, in certain embodiments of the invention, an authorization code may be required to permit reprogramming of the operating software of the device. In an embodiment of the invention, a software update program may be executed by the processor 102 to cause the computer program controlling the operating parameters of the device to be amended. As illustrated in the flowchart of FIG. 2, if the software update program is executed 202, the program instructions may attempt to receive a programming authorization code 204. This receipt may be as the result of a prompt displayed on the display 116 or may be received as part of the process of receiving software instructions uploaded to the device for reprogramming. In order to determine if the programming authorization code is valid, an embodiment of the invention may compare the code to a list of predetermined codes stored in the memory 112 or may execute software instructions which comprise a predetermined code authorization algorithm. For example, an embodiment of the invention may receive a numerical value contained in a collection of software instructions which comprise a software update and apply a predetermined mathematical equation to that numerical value. If the received code does not match the result of the equation, the embodiment of the invention may determine the received code to be invalid. If the received code is invalid the device may notify the user and stop the reprogramming process 206. Alternatively, if the authorization code is valid, the software may begin the reprogramming process 208. As will be described in more detail later herein, embodiments of the invention may comprise interactive games that encourage a user to participate actively in the exercise process (referred to herein as true exercise). The code verification process illustrated in FIG. 2 may also be used to validate the installation of a new or updated interactive game. In such a manner, access to the stimulation portions of the invention may be closely regulated in order to prevent inappropriate or potentially harmful control of the stimulator 104 output section of the invention. Such a method may be used to safeguard a software isolation boundary formed (described in more detail later herein) between the stimulation and biofeedback portions of the invention.

In use, embodiments of the invention may utilize the stimulation section 104 in conjunction with the probe 108 and electrodes 106 to provide a stimulation signal to a user. As the result of the configuration of the probe 108 and control of the stimulation section 104 by the processor 102, a controlled stimulation signal may be output to a user. Such a signal may function to cause a specific set of the user's muscles to contract in a way that provides the necessary stimulation to improve the conditioning of those particular muscles. The level and duration of stimulation may be adjustable in certain embodiments of the invention. One function of the stimulation provided by the invention is to allow a user to experience the contraction sensation that may result in an optimum level of conditioning of a user's pelvic floor muscles. As such, the process of stimulation could be thought of as a process of training the user's muscles to perform a conditioning exercise necessary to further improve the conditioning and resulting performance of the user's muscles. As used in this description, the term "stimulation" has a different meaning than that of "exercise." As used herein, "exercise" or "true exercise" means the voluntary control by a person of certain muscles to provide a desired result whereas, stimulation means that the muscles are stimulated electrically to cause a contraction of the muscle. With regard to pelvic floor muscles, one of the desired results of various combinations of stimulation and exercise is an improvement in a person's ability to control the various muscles regulating the flow of urine.

A user may instruct an embodiment of the invention using in input/output device 114 such as a switch or pushbutton, to start the process of providing a stimulation signal. In embodiments of the invention, a user may be able to select a particular stimulation regimen. For example, a user may select the duration and intensity of the desired stimulation process. Embodiments of the invention may be provided with limitations and warnings to the user in the event that the level and duration of stimulation may exceed a level that is safe or may prove to be uncomfortable to a user.

Figure 3:
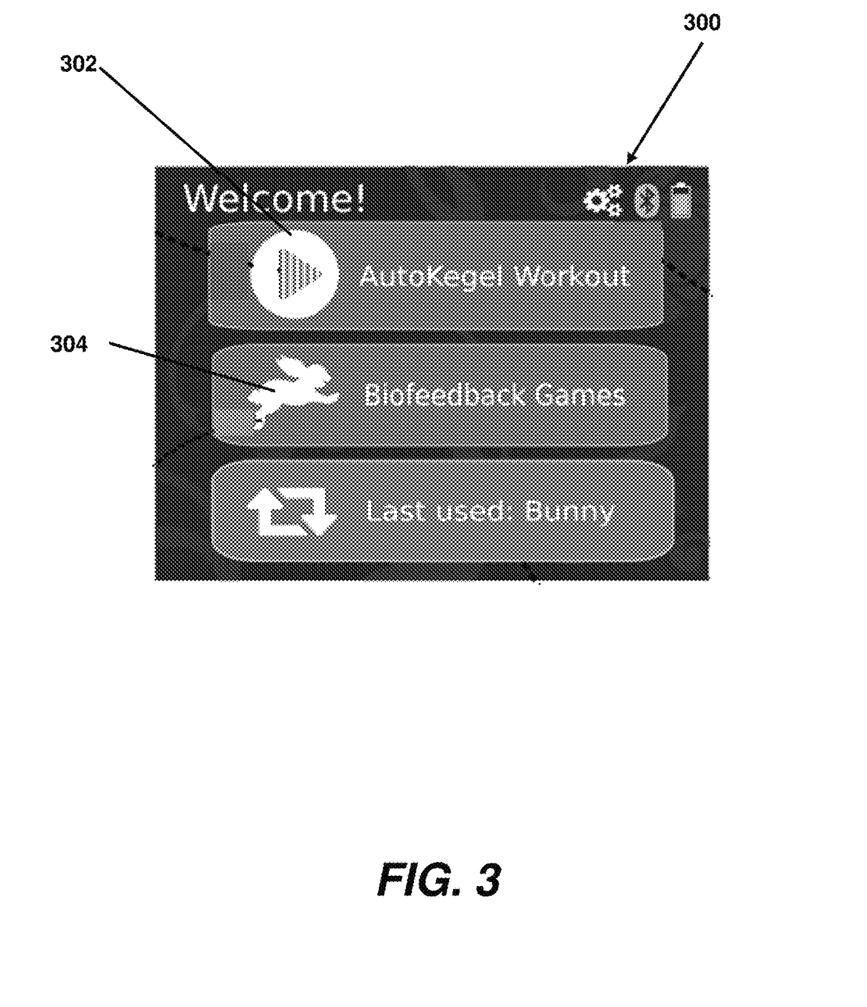
FIG. 3 is an example user interface of an embodiment of the invention.
Figure 4:
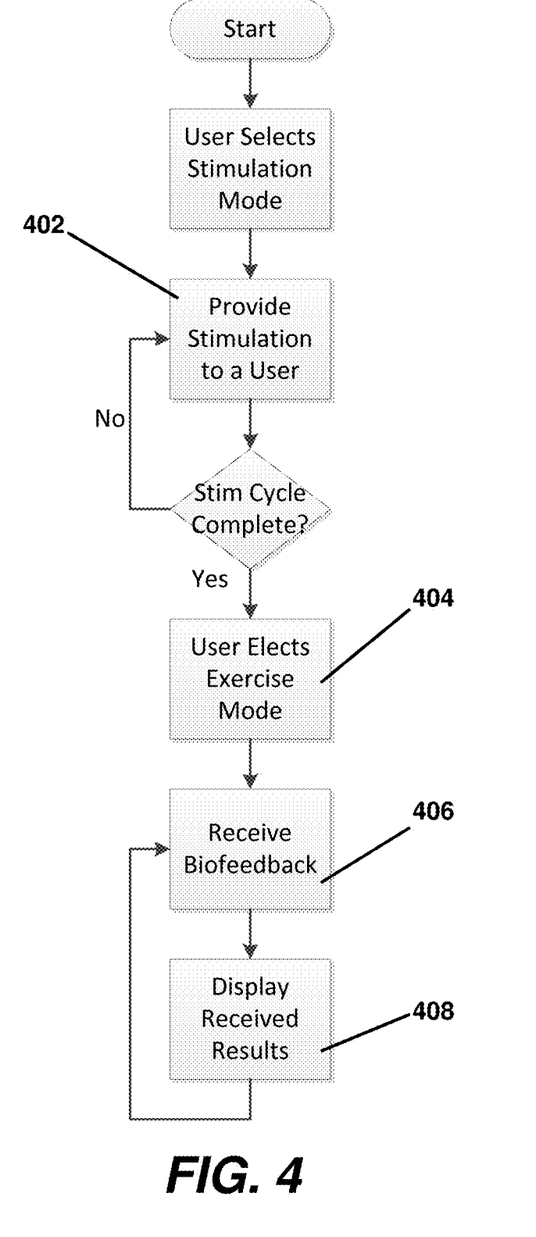
FIG. 4 is a flow chart of the steps performed by an embodiment of the invention.
Figure 5:
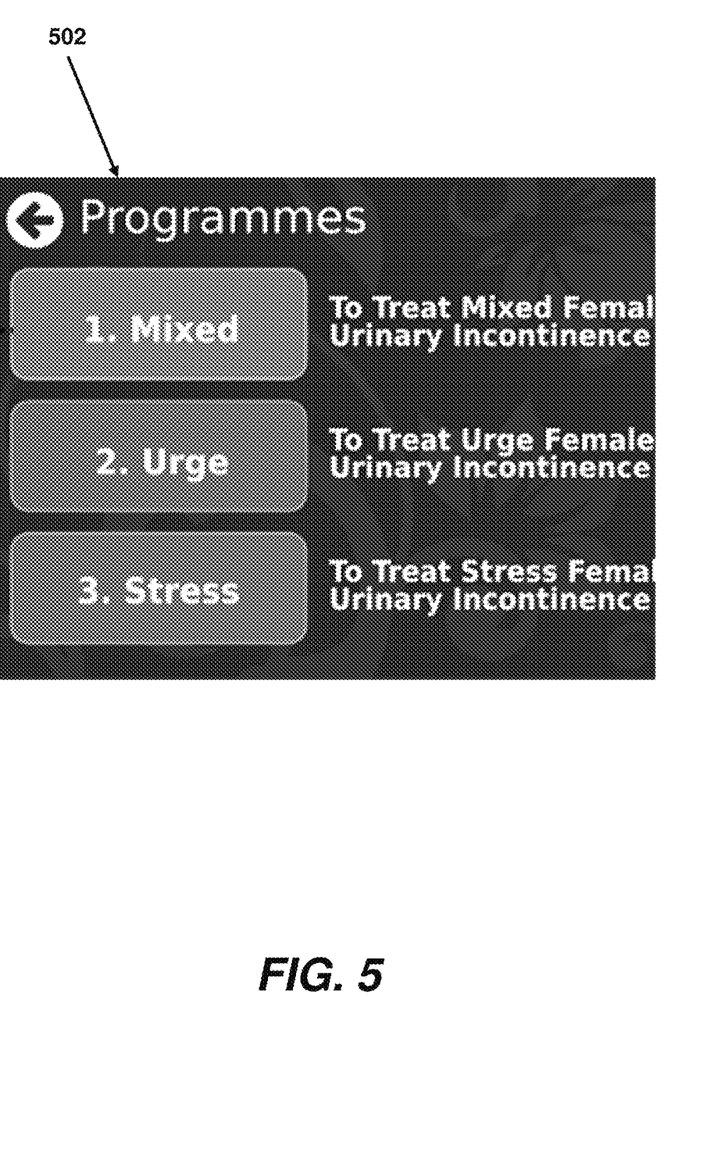
FIG. 5 is an example user interface of an embodiment of the invention.
Figures 6, 6A:
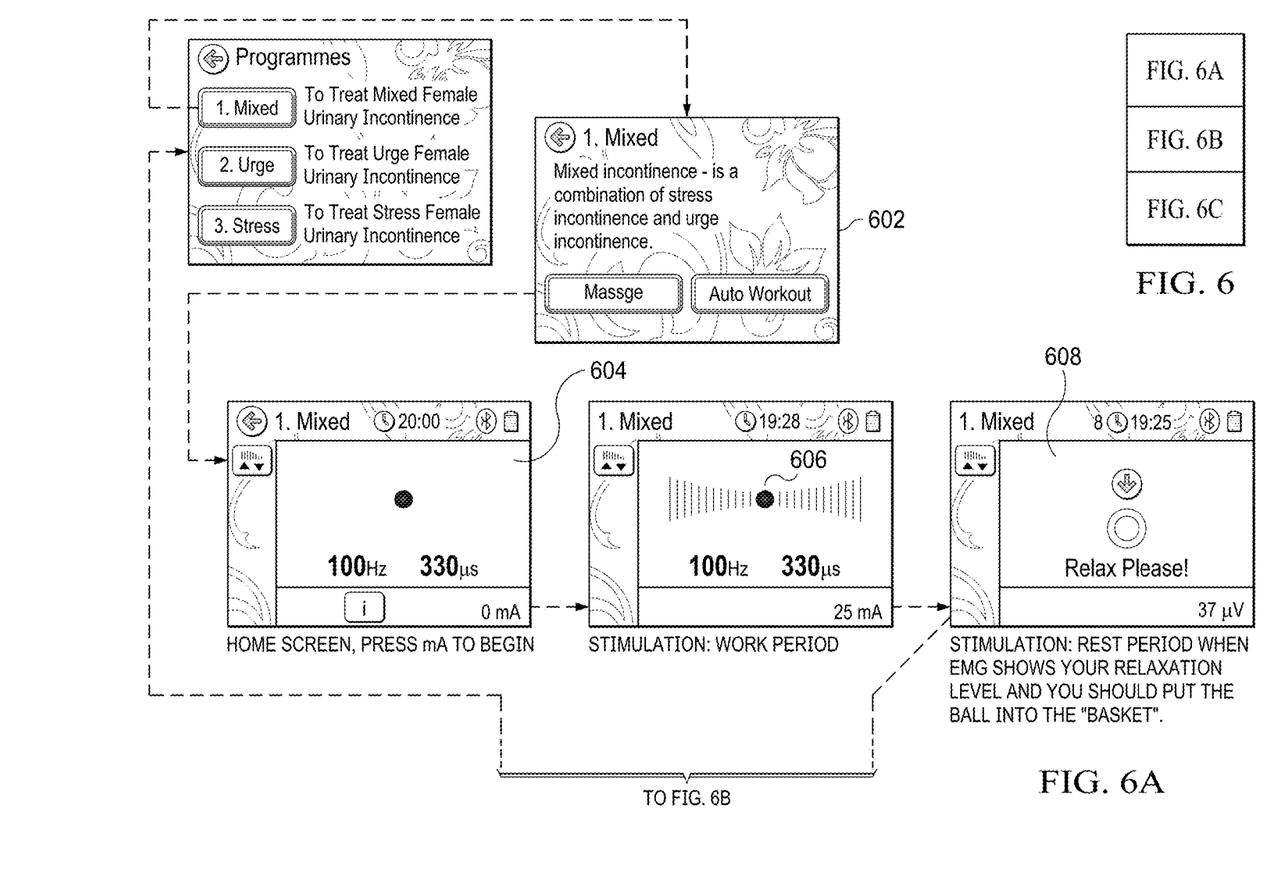
FIGS. 6A, 6B, and 6C together form an example of a plurality of user interfaces used in an embodiment of the invention.

In certain embodiments of the invention, a user may select between a stimulation mode and a biofeedback mode. An example of a user interface presenting such a selection is illustrated in FIG. 3. As is shown, a user may select stimulation 302 or biofeedback 304. As illustrated in to flow chart of FIG. 4, after a user selects stimulation from a menu similar to what is illustrated in FIG. 3, an embodiment of the invention may provide a stimulation signal to a user 402. When in such a mode, a user may be presented with a series of stimulation options. Referring to FIG. 5 which illustrates an example user interface, a user may be presented with menu 502 which provides options for various stimulation characteristics. For example, as illustrated a user may be presented with selections for the treatment of various types of female incontinence. As an example of how an embodiment of the invention may interact with a user, such a user may select a stimulation option from a main menu 300. When a user makes a menu selection, a second level of menu may be displayed 502. As illustrated, an embodiment of the invention may provide the user with additional choices in such a second level menu. Referring to FIG. 6 at 602, a user may select a massage stimulation option. When such an option is selected, a user may be presented with a user interface screen that displays the characteristics of the selected stimulation option 604. A user may elect to start the stimulation program corresponding to the selected option. When started, a user interface may provide feedback to the user in order to properly interact with the stimulation provided by the invention. For example, as illustrated, a user interface may provide an indication of the stimulation provided by the invention 606. In the illustrated example, a user may be required to relax their muscles during portions of the stimulation program. A user interface to provide the necessary feedback to a user is illustrated at 608. As illustrated, the stimulation signal may be removed and a user may be encouraged to relax their muscles to a certain level by a graphical illustration corresponding to a relaxed state. In the example shown, an indicator may be shown that moves across the user interface in response to a biofeedback input received by the invention that corresponds to a measured level of muscle relaxation. In such a manner, an embodiment of the invention may combine a stimulation portion 104 with a biofeedback portion 110.

In embodiments of the invention in which there is an electrical connection between the stimulation and biofeedback portions of the electronic circuitry, allowing the biofeedback portion of the invention to control the stimulation output could potentially result in injury to a user. The capability for such an interaction should be carefully regulated to prevent potentially harmful unauthorized software modifications. In order to provide a level of protection to the user that prevents the stimulation portion of the invention from interacting with the biofeedback portion of the invention, a software "firewall" may be formed to prevent such an interaction. As was described earlier herein, a requirement that software changes require an authorization code in order to be implemented may provide an additional layer of protection in that an unauthorized programmer may be prevented from having the level of access necessary to reprogram the processor 102 to overcome the software firewall. In such a manner, an undesired interaction that could result from unauthorized programming may be prevented.

Figure 7:
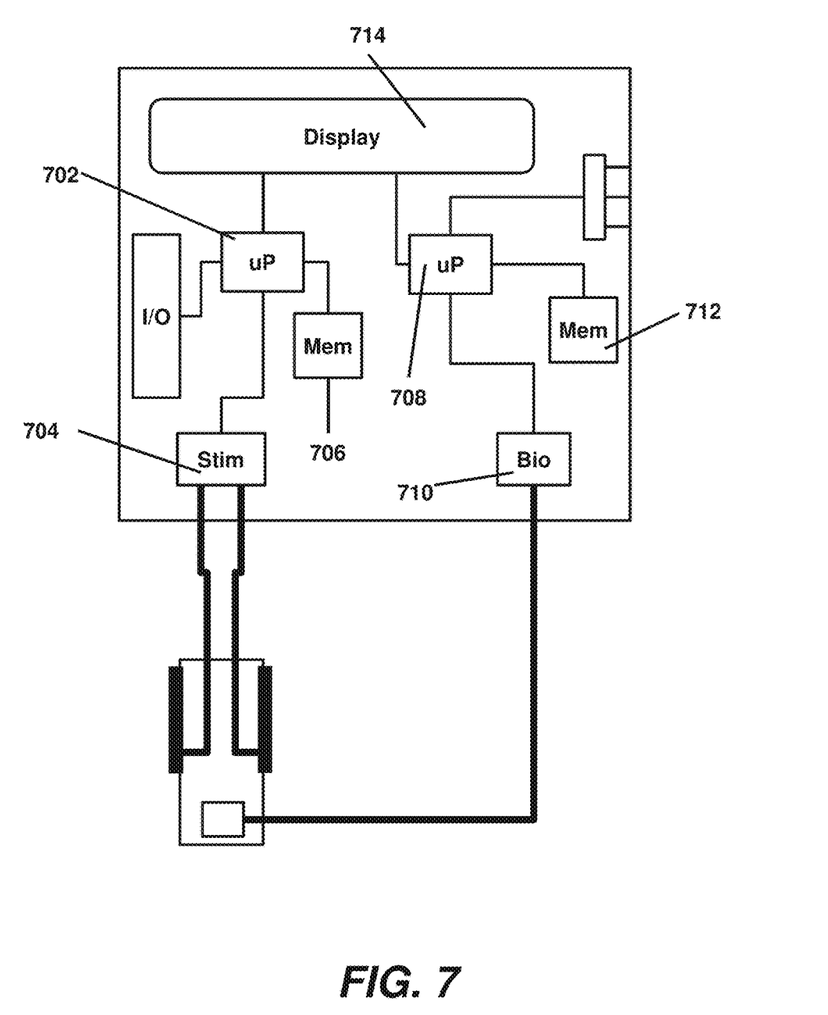
FIG. 7 is a block diagram illustrating an alternative embodiment of the invention.

In other embodiments of the invention, a physical separation (firewall) between the stimulation portion and the biofeedback portion may be implemented. Such an embodiment is illustrated in FIG. 7. In such an embodiment, a first processor 702 may be in electrical communication with a stimulation portion 704. Software instructions may be contained in a memory 706 that is in electronic communication with the first processor 702. As illustrated, a second processor 708 may be in electronic communication with a biofeedback receiver 710 and a second memory 712. In such a configuration, an embodiment of the invention may have two isolated control sections such that there is a separation between the stimulation and biofeedback portions of the invention. Such a separation may further ensure that there is no undesired interaction between the stimulation and biofeedback portion of the invention. As illustrated, in embodiments of the invention, certain components such as a display portion 714 may be in communication with both the first processor 702 and the second processor 708 while retaining the isolation between the stimulation and biofeedback portions of the invention.

Figure 8:
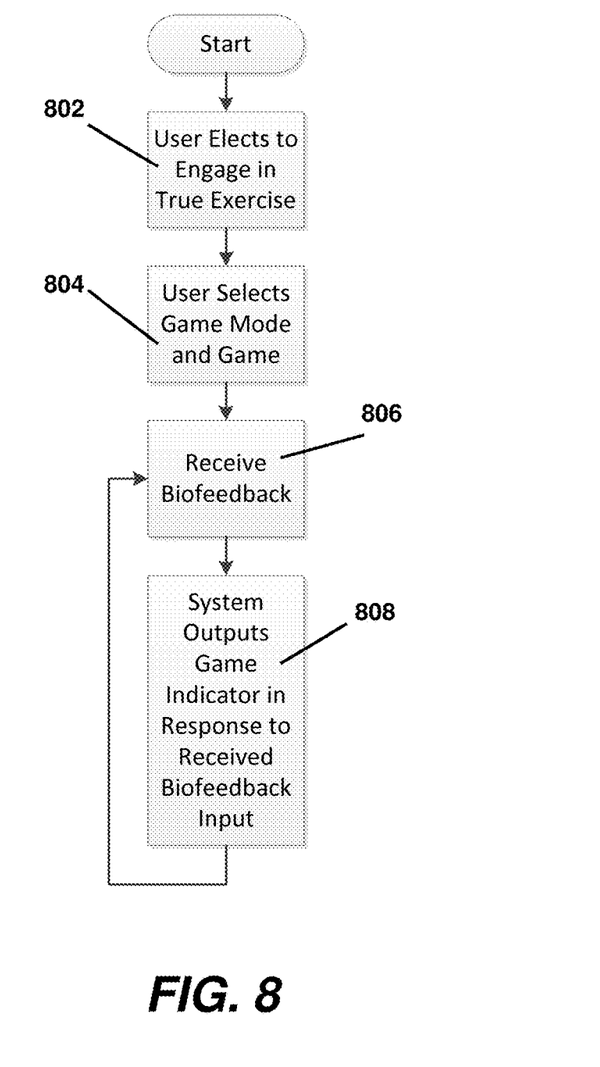
FIG. 8 is a flow chart of the steps that a user may take when interacting with an embodiment of the invention in order to engage in a biofeedback game.

When the user desires to switch from stimulation to true exercise as defined herein, that user may elect to interact solely with the biofeedback portion of the invention. Referring again to the flowchart of FIG. 4, a user may select a biofeedback only operation 404. As illustrated, an embodiment of the invention may then receive biofeedback input data from the biofeedback receiver 110 in step 406. In certain embodiments of the invention, biofeedback results may be displayed to a user 408 in order to guide that user's performance of a series of exercise steps. As shown in the flowchart of FIG. 8, a user may elect to engage in true exercise 802. In step 804, such a user may select an exercise game from one or more such exercise games provided by an embodiment of the invention. During the process of a user's playing such a game, an embodiment of the invention may receive biofeedback data from the biofeedback receiver 102 in step 806. In order to provide feedback to a user, an embodiment of the invention may display a game indicator in response to the received input in step 808.

Figure 6B:
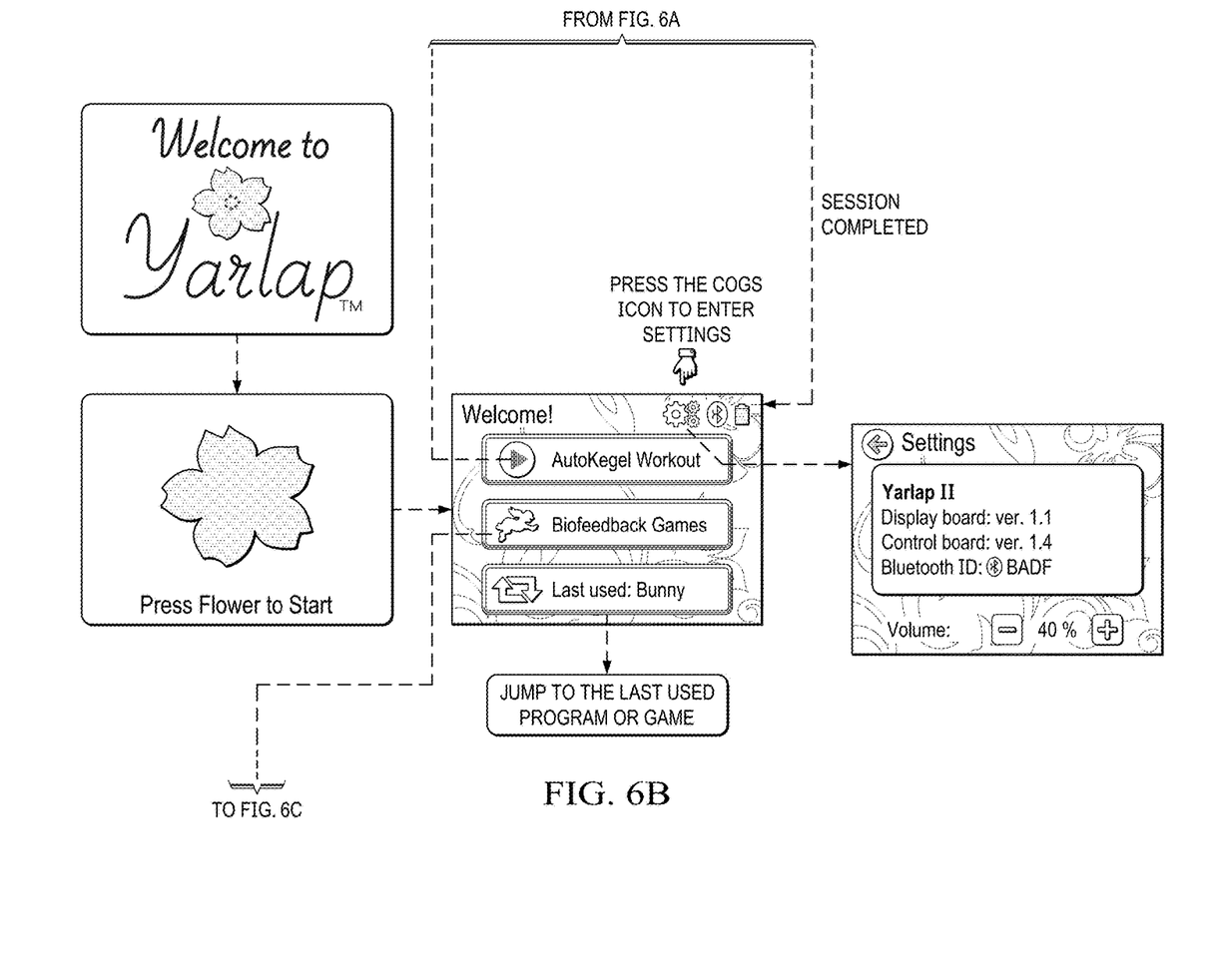
Figure 6C:
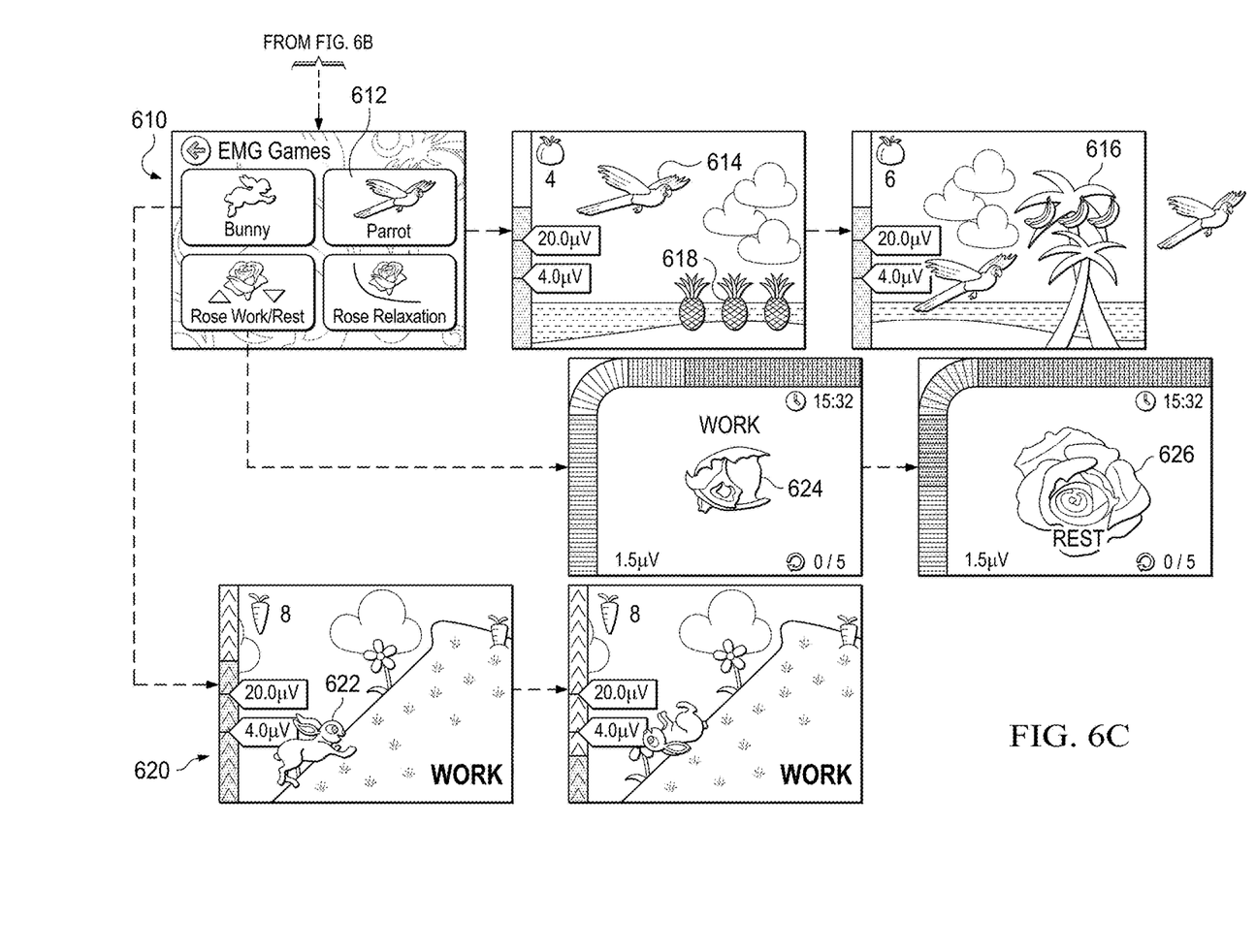

As with many forms of exercise, keeping the person performing the exercise engaged with the exercise may be facilitated by the use of games or similar competitive tasks. In such methods, providing a user the ability to compete against a series of predetermined tasks or alternatively, against another person, may distract the focus of such a person of the exercise itself and onto the competitive challenge provided by the game. Using such a technique, a user may find it easier and less tedious to perform the desired exercise. In embodiments of the present invention, the exercise goal is to encourage the user to perform a series of muscle contractions and releases of sufficient duration and intensity to produce an improvement in the muscle condition of the pelvic floor muscles of the person performing the exercise. As illustrated in FIG. 6, a user may be presented with a selection of various games 610. In the illustrated embodiment, the selection of games is intended to provide a series of exercise steps directed towards a specific goal. As illustrated, a first game 612 may involve encouraging a user to contract and release their muscles in a specific pattern. In the illustrated example, this is accomplished by displaying a bird 614 that appears to fly through the air. The bird can be made to rise and fall according to the biofeedback received by an embodiment of the invention. In such an embodiment, a rise of the displayed bird 614 may represent a user's increase in the strength of their muscle contraction. Conversely, the bird 614 may fall in response to the user's relaxing their muscles. As the bird 614 appears to fly through the air, a series of obstacles may be presented such that the user must contract their muscles to prevent the bird from colliding with the presented obstacle. Thus, to encourage the user to repeatedly contract their muscles, the series of obstacles 616 (illustrated as trees) may be presented in series according to how long it is desired to require the user to tighten their muscles. Similarly, in order to get the user to relax or vary the strength of the contraction of their muscles, a series of objects or prizes may be displayed 618 (here illustrated as pineapple shapes). Such prizes may be positioned at various levels of the display to encourage a user to maintain a predetermined level of contraction in order to cause the bird shape to pass over the prize.

As illustrated at 620, in other embodiments of the game a user may be encouraged to tighten their muscles to cause a displayed character to rise or fall along an incline as illustrated 622. As shown, the incline may be illustrated as an increasingly steep hill. The user may be encouraged to tighten or relax their muscles to cause the character to move up and down the incline or to hold the character in a certain position. These movements may cause the user to be aware of their ability to partially contract or relax their muscles. Similarly, in another embodiment of such a game, a user may be presented with a shape which can illustrate a contracted or relaxed muscle. As illustrated in FIG. 6 at 624, a flower may be shown as closed when a user's muscles are contracted or open 626 when that same user is causing their muscles to relax.

Figure 9:
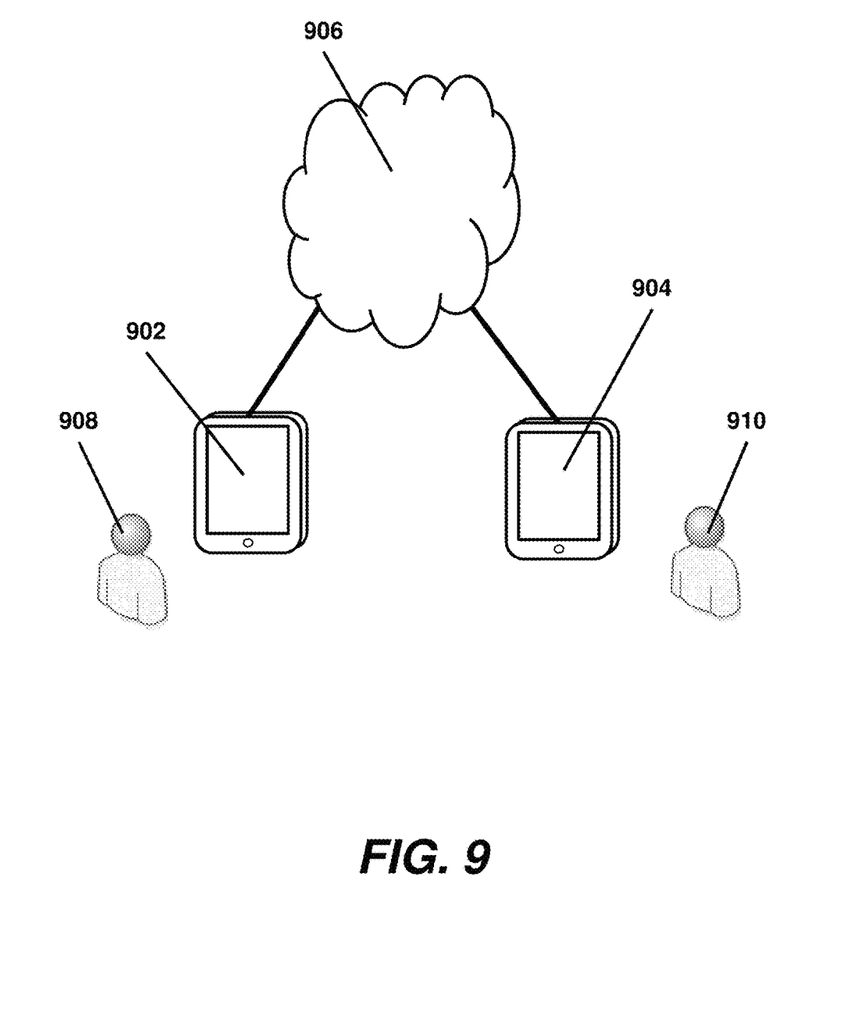
FIG. 9 is a diagram illustrating embodiments of the invention in electronic communication with each other to allow users to compete against each other.

In order to further engage a user, embodiments of the invention may be configured to communicate with other users as illustrated in FIG. 9. As shown, a first device 902 may be placed in electronic communication with a second device 904. As illustrated, the connections are formed using a connection through the internet 906. One ordinarily skilled in the art will understand that the connection from the devices 902 and 904 may involve Wi-Fi, a wired connection, cellular data or other connection methods that may become available. When connected, the user of the first device 908 and the user of the second device 910 may engage in a competitive game play mode in which the first and second user may compete against each other by performing contraction and relaxation movements such that they earn points or progress through a game more quickly than the other player in order to win the competitive game. As with single user game play modes, this embodiment of the invention may serve to further encourage a user to perform conditioning exercises in order to improve their muscle condition to prevent or improve conditions such as incontinence.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A system for conditioning the pelvic floor muscles of a female user comprising:
    a first processor;
    a first memory in electronic communication with the first processor;
    a second processor;
    a second memory in electronic communication with the second processor;
    a display in electronic communication with the first processor and the second processor;
    an electronic stimulator in electronic communication with the first processor, but not the second processor;
    a biofeedback receiver in electronic communication with the second processor, but not the first processor;
    a probe configured to be placed in contact with the pelvic floor muscles comprising:
        a plurality of electrodes positioned on the probe and configured to provide electrical stimulation to the pelvic floor muscles, wherein each of the electrodes are in electrical communication with the electronic stimulator and are not in electrical communication with the biofeedback receiver;
        a transducer positioned on the probe and configured to detect muscle contractions of the pelvic floor muscles, wherein the transducer is in electronic communication with the biofeedback receiver and is not in electronic communication with the electronic stimulator;
    a first set of software instructions stored in the first memory that when executed by the first processor configure the first processor to:
        receive from the user, a selection corresponding to the initiation of electronic stimulation, and
        in response to the selection, cause the electronic stimulator to produce a series of electrical stimulation signals that are communicated to the plurality of electrodes;
    a second set of software instructions stored in the second memory that when executed by the second processor configure the second processor to:
        receive from the user, a selection corresponding to the initiation of biofeedback monitoring, and
        in response to the selection, cause the biofeedback receiver to monitor a signal from the transducer,
        receive the signal from the biofeedback receiver and causing an indication of the signal level to be displayed at the display, and
        display at the display, a series of indicators prompting the user to input a signal to the transducer, and
        a firewall adapted to prevent the production of any electrical stimulation signals at the electrodes during the biofeedback monitoring.

2. The system of claim 1, further comprising:
    a second device;
    an electronic communications interface in electronic communications with at least the second processor, the electronic communications interface comprising at least one of a Wi-Fi transceiver, an Ethernet interface, a Bluetooth transceiver, or a cellular data transceiver;
    the second software instructions that when executed by the second processor in communication with the electronic communications interface cause the second processor to:
        establish an electronic connection to the second device using the electronic communications interface;
        communicate a signal corresponding to the signal received from the biofeedback receiver to the second device;

receive a signal from the second device that corresponds to a biofeedback signal received by the second device; and display at the display, an indication of the received signal.

3. The system of claim 1, further comprising:

an external display;

an electronic interface configured to enable the system to be placed in electronic communications with the external display; and the second software instructions cause a signal to be provided to the electronic interface which causes a user interface to be displayed on the external display.

4. The system of claim 1, wherein the firewall comprises additional software instructions, that when executed by the first or second processor, cause the first or second processor to:

receive an authorization code;

receive program instruction steps;

determine if the authorization code is correct using a predetermined rule;

when the authorization code is determined to be correct, causing the first or second processor to load the program instruction steps into the second memory by means of an interface connection.

5. The system of claim 4, further comprising:

an external memory device; and wherein the interface connection is limited to a wired connection from the external memory device.

6. The system of claim 1 further comprising additional software instructions stored in the second memory that when executed by the second processor configure the second processor to:

receive from a user, a selection corresponding to the selection of a biofeedback game; and in response to the selection, cause a game user interface to be displayed at the display;

wherein the game user interface comprises a bird in flight, wherein the height of the bird in the game user interface is increased as the level of signal received from the transducer increases and the height of the bird in the game user interface is decreased as the level of signal received from the transducer decreases.

7. The system of claim 6 wherein the game user interface further comprises a series of obstacles and a series of prizes each located at various heights, wherein the height of the prizes and obstacles is depicted to reflect levels of signals corresponding to a desirable muscle activity.

* * * * *